United States Patent [19]

Shibuya et al.

[11] Patent Number: 5,741,652
[45] Date of Patent: Apr. 21, 1998

[54] ANTI-HUMAN TYPE IV COLLAGEN ANTIBODIES AND USE THEREOF

[75] Inventors: Akitaka Shibuya, Sagamihara; Shunji Saitoh, Machida; Toshio Takahashi, Yokohama; Masanori Kamei, Yokohama; Naoko Maruo, Yokohama, all of Japan

[73] Assignees: Tosoh Corporation, Shinnanyo; Morinaga & Co., Ltd., Tokyo, both of Japan

[21] Appl. No.: 536,740

[22] Filed: Sep. 29, 1995

[30] Foreign Application Priority Data

Sep. 30, 1994 [JP] Japan .................................. 6-237962

[51] Int. Cl.$^6$ .................................................. G01N 33/53
[52] U.S. Cl. .......................... 435/7.1; 435/7.2; 435/7.92; 435/7.94; 435/975; 435/7.95; 436/63; 530/388.2; 530/389.2; 530/387.1; 530/387.9; 530/388.1
[58] Field of Search ....................... 435/7.1, 7.72, 435/7.92, 7.94, 7.95, 975, 240.27; 436/63; 530/388.2, 389.2, 387.1, 387.9, 388.1

[56] References Cited

U.S. PATENT DOCUMENTS

| 4,391,904 | 7/1983 | Litman et al. | |
|---|---|---|---|
| 5,316,914 | 5/1994 | Oshima et al. | 435/7.94 |

FOREIGN PATENT DOCUMENTS

| 0 401 370 | 12/1990 | European Pat. Off. |
| 63-63971 | 3/1988 | Japan . |
| 63-325663 | 12/1988 | Japan . |
| 2-1553 | 1/1990 | Japan . |
| 90 07116 | 6/1990 | WIPO . |

OTHER PUBLICATIONS

Schuppan et al., "Raidoimmuninoassay for the Carboxy–terminal Cross–linking Domain of Type IV (Basement Membrane) Procollagen in Body Fluids", J. Clin. Invest., vol. 78, pp. 241–248, (1986).
Sage et al., "Structural Studies in Human Type Collagen", Journal of Biological Chem. vol. 254, No. 19, pp. 9893–9900, (1979).
Obata et al. (1989) Clinica Chimica Acta 181:293–904.
Goding, J. W. (1983) "Monoclonal Antibodies: Principles and Practice", Academic Press, Inc., Orlando, pp. 7–10 and 250–161.

Hogemann et al., "7S Collagen: A Method for the Measurement of Serum Concentrations In Man", Clinica Chimica Acta, vol. 144, pp. 1–10, (1984).
"Hepatic Fibrosis and Cytokines, etc.", Molecular Medicine, vol. 31, No. 2, (1994).
IV Type Collagen 7S Kit Nippon DPC.
Yamada et al., "Clinical Significance of Serum 7S Collagen in Various Liver Diseases", Clin. Biochem., vol. 25, pp. 467–470, (1992).
Risteli et al., "7–S Collagen: Characterization of an Unusual Basement Membrane Structure", Eur. J. Biochem., vol. 108, pp. 239–250, (1980).
Manual for "Panassay IV/c For Blook Serum Type IV Collagen Measurement, Daiichi Pure Chemicals".
Obata et al., "One Step Sandwich Enzyme Immunoassay for Human Type IV Collagen Using Monoclonal Antibodies", Clinica Chimica Acta., vol. 181, pp. 298–304, (1989).
Timpl et al., "A Network Model for the Organization of Type IV Collagen Molecules in Basement Membranes", Eur. J. Biochem. vol. 120, pp. 203–211, (1981).
Murawaki et al., "Serum Type III Proco. Pep., Type IV Colla. 7S Domain, Cent. Triple–Helix Type IV Coll. & Tissue Inhib. Metalloproteinases . . . ", Hepatology, vol. 20, No. 4, pp. 780–787, (1994).
Risteli et al., "Sensitive Radioimmunoassays for 7S Collagen and Laminin: Application to Serum and Tissue Studies of Basement Membranes", Analyt. Biochem. vol. 113, pp. (1981).
Hahn et al., "Distribution of Basement Membrane Proteins in Normal and Fibrotic Human Liver: Collagen Type IV, Laminin, and Fibronectin", Gut, vol. 21, pp. 63–71, (1980).
Niemela et al., "Type IV Collagen and Laminin–Related Antigens In Human Serum In Alcoholic Liver Disease", Eur. J. of Clinical Investigation, vol. 15, pp. 132–137, (1985).

*Primary Examiner*—Paula K. Hutzell
*Assistant Examiner*—Heather A. Bakalyar
*Attorney, Agent, or Firm*—Foley & Lardner

[57] ABSTRACT

A method for one-step immunoassay of human type IV collagen, which uses a carrier immobilizing monoclonal antibody against human type IV collagen and a labelled polyclonal antibody against human type IV collagen, as well as a kit therefor and monoclonal antibodies which are particularly suited therefor.

It is possible to accurately and quickly measure human type IV collagen in blood serum, for example, and obtain measurement results which accurately reflect pathological conditions.

22 Claims, 4 Drawing Sheets

ANTI-HUMAN TYPE IV COLLAGEN ANTIBODIES AND USE THEREOF

BACKGROUND OF INVENTION

1. Field of the Invention

The present invention relates to monoclonal antibodies against human type IV collagen, and to an immunoassay method and kit for measuring human type IV collagen using said monoclonal antibody.

2. Related Art

Collagen is present in connective tissues, and to date 15 genetically different types have been reported, including type I, II, III, IV, etc. These types have been found to have organ specificities, with type I and III collagen plentiful in the bones and skin, and type IV collagen contained in the basement membranes of the blood vessel skin, digestive organs, muscles, nerve fibers, nephroglomeruli, lungs, etc.

Type IV collagen is composed of 4 parts, the amino terminal 7S domain, the carboxyl terminal NC1 and NC2 domains, and a triple helical domain (TH domain) wherein the intermediate peptides are combined in a helix form.

Hepatic fibrosis has been reported to occur in an early stage of liver cirrhosis (Molecular Medicine, Vol. 31, No. 2, 1994; Special issue: Hepatic fibrosis and Cytokines, etc.). In recent years, hepatic fibrosis markers have emerged into clinical application for liver cirrhosis, and thus it has become possible to take continuous, frequent measurements in a non-invasive manner without liver biopsy, with great usefulness for the analysis of liver disease.

The major hepatic fibrosis marker is the extracellular matrix (ECM), and the related enzymes and degradation products may be used as markers reflecting the degree of fibrosis. Since type IV collagen is produced and secreted out by endothelial cells and liver cells, especially Ito cells, from the early stages of hepatopathy, its increase is taken to reflect hepatic fibrosis. In addition, a portion of the type IV collagen produced in the liver enters the blood vessels and therefore type IV collagen in the blood serum may be used as an index of hepatic fibrosis.

Two methods are commonly known for measuring type IV collagen in the blood serum. Corresponding measuring kits for them are commercially available. The first method is a competitive method using a radioactive isotope, wherein the 7S domain of type IV collagen obtained by purifying placenta-extracted type IV collagen by collagenase treatment is used as the antigen, and this 7S domain is labelled with $^{125}$I as the labelled antigen while the 7S domain is injected into rabbits to prepare antibodies against the 7S domain of type IV collagen (type IV collagen/7S kit manual: Nippon DFC Corp.; Yamada, et al., Clin. Biochem. Vol. 25, p. 467–470, 1992; Risteli, et al., Eur. J. Biochem. Vol. 108, p. 239–250, 1980).

The second method is the so-called one-step sandwich enzyme immunoassay (EIA) method which uses a monoclonal antibody against pepsin-solubilized human type IV collagen and a monoclonal antibody against the 7S domain of human type IV collagen (Manual for "Panassay IV/C" for blood serum type IV collagen measurement; Daiichi Pure Chemicals; Japanese Unexamined Patent Publication No. 2-1553; Clinical Chimica Acta 181, p. 293–304, 1989).

However the radioimmuno assay method described above requires careful handling of radio isotope and complicated procedures. For example, special equipment and faculties meeting the regal regulation are necessary, which restricts the locations permitting the measurement. The disposal of waste liquid is also a matter of concern and attention has to be paid for avoiding hazardous irradiation effects on human health. Furthermore, commercial kits for this type of assay involve these problems as well as the fact that the reaction time is as long as 16–24 hours is required, and 200 μl of sample is required per test, which is substantially larger than for common blood test.

On the other hand, the above described commercial kit for one-step sandwich EIA requires 1 hour for the reaction, which is rather long for one-step EIA.

Furthermore, those two types of commercial assay kits described above are both manual assay kits, and consequently they cannot be applied for automatic measurement as is as commonly desired object in the field of clinical diagnosis.

Moreover, in the field of clinical diagnosis there are usually desired measuring methods with improved intra- and inter-assay reproducibilities (CV %), assay sensitivity, etc., in which the results of actual measurement with a patient's serum accurately reflect the pathological state of the patient.

SUMMARY OF THE INVENTION

In general, the use of monoclonal antibodies improves the repeatability, reproducibility and assay sensitivity and gives positive results of actual measurement of a patient's serum which accurately reflect the pathological condition of the patient. As a result of a study by the present inventors, from the point of view presented above, regarding immunoassays of human type IV collagen which has been attracting attention as a marker for hepatic fibrosis, the inventors reached the conclusion that the above-mentioned problems cannot be overcome by simply using two different types of monoclonal antibodies, given the fact that type IV collagen detected in blood serum as the object of measurement is not necessarily a simple, pure substance, but has been split between the 7S domain and the NCI domain by collagenase (Timpl, et al., Eur. J. Biochem. 120, p. 204–211, 1981).

Then, as a result of further diligent research, the inventors established a novel method for determining human type IV collagen, by which the results of measurement reflect the condition of patients, the handling of reagents and the measuring procedure are simple, there are no problems of effects on the body or disposal of waste liquid, and the measurement may be carried out with a small amount of sample in a short period of time.

In other words, the present invention provides an method for immunoassay of human type IV collagen in a sample, which is characterized by using a monoclonal antibody against human type IV collagen and a labelled polyclonal antibody against human type IV collagen.

The present invention also provides a monoclonal antibody against human type IV collagen for use in the above-mentioned immunoassay method, which monoclonal antibody has the following properties:

(1) It is raised against the pepsin-solubilized human type IV collagen;

(2) It binds to the 7S domain of human type IV collagen but not to other domains;

(3) it does not bind to human type I, type III and type V collagen;

(4) When analyzed by SDS-polyacrylamide gel electrophozesis (PAGE) under reduced condition, the molecular weight of the heavy (H) chain is about 51,000 and the molecular weight of the light (L) chain is about 28,000; and (5) It is IgG1κ subtype.

The present invention further provides a monoclonal antibody with the following properties:

(1) It is raised against the pepsin-solubilized human type IV collagen;

(2) It binds to domains other than the 7S domain human type IV collagen but does not bind to the 7S domain;

(3) It does not bind to human type I, type III and type V collagen;

(4) When analyzed by SDS-PAGE under reduced condition, the molecular weight of the heavy (H) chain is about 50,000 and the molecular weight of light (D) chain is about 27,000; and (5) It is IgG2κ subtype.

DETAILED DESCRIPTION

Figure 1:
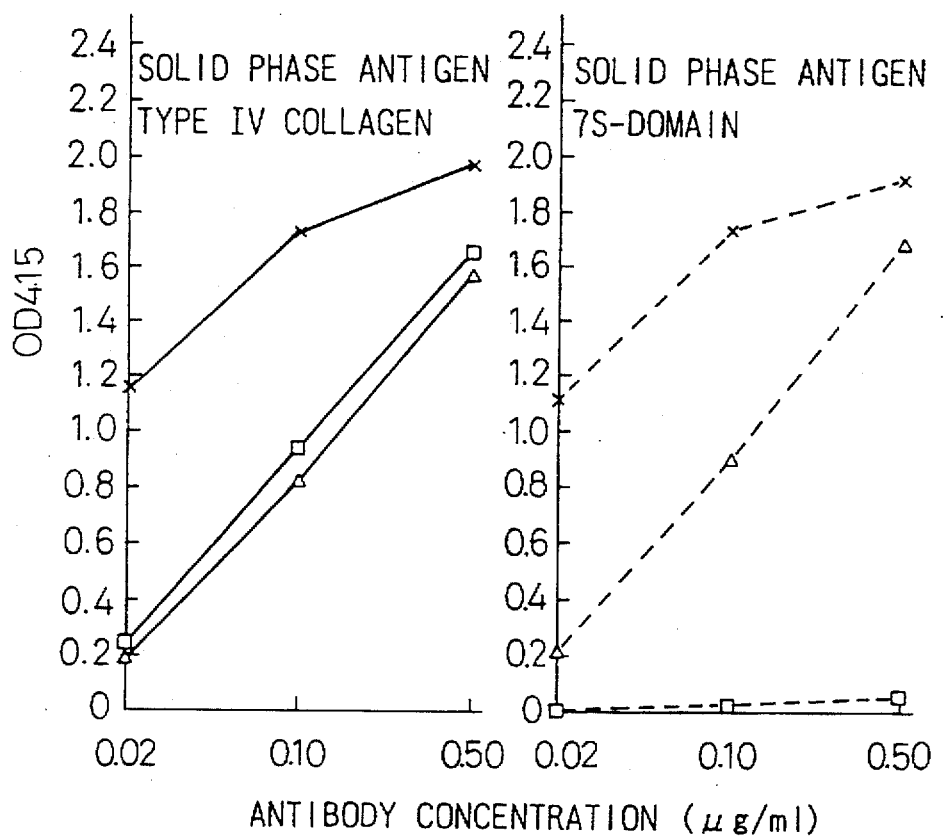
FIG. 1a is a graph showing the results of testing the binding sites of the monoclonal antibodies 238 and 67 and polyclonal antibody of the present invention, on the human type IV collagen molecule.
FIG. 1b is a graph showing the results of testing the binding sites of the monoclonal antibodies 238 and 67 and polyclonal antibody of the present invention, on the 7S domain of human type IV collagen molecule.

According to the present invention, the method for measuring human type IV collagen in samples does not use a radioactive isotope, and consequently does not require special equipment or devices which impose limitations on the location where the measurement may be made, while disposal of the waste water is simple and there is no effect on the body. There are other advantages as well, as only a small amount of blood is necessary, making the method suitable for automation, and the reaction time is as short as 40 minutes.

Furthermore, as will be demonstrated in the examples which follow, the method of the present invention gives results which accurately reflect the condition of patients. That is, there is close correlation between the presence of hepatic fibrosis observed in liver biopsy and the human type IV collagen examination results obtained by the method of the present invention, and more so than with examination using commercially available kit.

The effect of the present invention is particularly exhibited when a monoclonal antibody is used which binds specifically to the 7S domain of human type IV collagen. As mentioned above, type IV collagen also exists in the serum in the form of fragments produced by body proteases such as collagenase, and the 7S domain is relatively stable in the body among these fragments.

Consequently, the results of a measurements which reflect the conditions of patients may be obtained by using a monoclonal antibody specific to the 7S domain of human type IV collagen as the primary antibody binding to the carrier, to capture the human type IV collagen or fragments thereof containing the 7S domain, and then detecting the captured human type IV collagen or fragments thereof containing the 7S domain using a polyclonal antibody (secondary antibody) with a relatively wide specificity range which binds to the human type IV collagen or fragments thereof containing the captured 75 domain.

If, instead, a monoclonal antibody is used as the secondary antibody, sometimes only a portion of the type IV collagen or fragments thereof captured by the primary antibody will be detected.

Furthermore, if it is attempted to use two types of polyclonal antibodies to shorten the measuring time by a one-step method, accuracy and sensitivity may be lost.

The polyclonal antibody and menoclonal antibody of the present invention may be prepared according to conventional methods. As examples of concrete methods, a method of producing polyclonal antibodies is given in Example 1, and a method of producing monoclonal antibodies is given in Example 2.

In the immunoassay method of the present invention, first a monoclonal antibody specific to the 7S domain of human type IV collogan is immobilized on a carrier to be used as the primary antibody. A solid carrier is preferred as the carrier, and any desired solid carrier which is common in immunoassays may be used including high molecular weight carriers such as styrene and polystyrene molded into a desired size and shape, as well as inner walls of reaction containers formed such appropriate materials.

The immobilization of the monoclonal antibody on the carrier may be carried out by a common method, such as by contacting the monoclonal antibody with the carrier in a buffer solution, for example a boric acid buffer solution. Another method, for example, is one in which an antibody against the monoclonal antibody to be used is first immobilized on a carrier, and this is then contacted with the monoclonal antibody. The monoclonal antibody used as the primary antibody is preferably an antibody which binds specifically to the 7S domain of human type IV collagen, for the reasons explained above under "Effect of the Invention", and in concrete terms, the monoclonal antibody 67 produced by the hybridoma COL-IV-67 (FERM P-14561) is preferred. The hybridoma COL-IV-67 was deposited with National Institute of Bioscience and Human-Technology Agency of Industrial Science of Technology, 1–3, Higashi 1-chome, Tsukuba-shi, Ibaraki, Japan, as FERM P-14561 on Sep. 27, 1994, and transferred to an international deposition under the Budapest treaty as FERM BP-5240 on Sep. 25, 1995.

Meanwhile, the polyclonal antibody against human type IV collagen is labelled, preferably with a non-radioactive labelling system, as the secondary antibody. The non-radioactive labelling used may be enzyme labelling, fluorescent labelling or optical labelling such as luminescent labelling. Enzyme labelling is preferred, and for example alkaline phosphatase (ALP), β-D-galactosidase, horseradish peroxidase, or the like may be used as the labelling enzyme.

The detection of these enzymes may be accomplished using their respective enzyme substrates, namely 4-methylumbelliferyl phosphate (4-MUP), 2-nitrophenyl-β-D-galactoside, a combination of hydrogen peroxide and 3,3'-5,5'-tetramethylbenthidine, etc. These enzyme substrates change color or luminescence by the action (e.g. cleavage) of the enzyme, and may thus be detected.

A common method may be used to conjugate the secondary antibody and the enzyme label, and for example, a commercial thiol-based cross-linking reagent may be used to introduce thiol groups into both the labelling substance and the antibody, which are then combined together by S—S bond.

In the one-step method of the present invention, the above-mentioned carrier with primary monoclonal antibody immobilized, the above-mentioned labelled secondary polyclonal antibody and the testing sample are mixed together and incubated, to bind the human type IV collagen molecules in the testing sample to the primary monoclonal antibody immobilized on the carrier, and to bind the labelled secondary polyclonal antibody to the collagen molecules.

In this manner, the labelled secondary polyclonal antibody is immobilized on the carrier through the primary antibody immobilized on the carrier and the type IV collagen in the sample, in an amount which reflects the amount of type IV collagen in the sample.

This reflected amount becomes apparent upon incubation preferably in a buffer solution, for example Tris-HCl or phosphate buffer solution, for 10 to 120 minutes, preferably 10 to 40 minutes, at 15° C. to 40° C., preferably 20° to 37° C., or at room temperature, for example.

Next, the bound labelled carrier and the unbound labelled carrier are separated. In cases where the carrier is a solid carrier, this separation may be easily accomplished by solid-liquid separation. If a given known amount (in excess) of the labelled antibody (secondary antibody) has been used, then the labelling which is either bound or unbound to the carrier, or both, may be measured. On the other hand, if an arbitrary amount (unknown and in excess) of the labelled antibody has been used, then the amount of labelling which has bound to the carrier may be detected and measured. The detection of the labelling bound to the carrier is preferably accomplished by a detection reaction after washing the carrier with a washing solution, for example distilled water containing a surfactant, etc. or an appropriate buffer solution, to remove the unbound labelled antibody. The detection may be carried out according to a common method, depending on the type of labelling.

The present invention also provides an assay kit for type IV collagen. The kit includes at least a carrier on which monoclonal antibody against human type IV collagen has been immobilized, or the monoclonal antibody and a carrier for its immobilization, and a polyclonal antibody against human type IV collagen which has been labelled. The monoclonal antibody-immobilized carrier and the labelled polyclonal antibody are the same as described in detail above, and specific cases will be given in the following examples. The kit may also include a standard solution of human type IV collagen for calibrating the assay together with directions for its handling.

EXAMPLES

The present invention will now be more fully explained by way of the following examples.

Example 1

Preparation of specific anti-human type IV collagen antibody (polyclonal antibody)

(a) Preparation of human type IV collagen

The IV collagen was prepared from human placenta following the method of Sage, et al. described in J. Biol. Chem., 254, 9893–9900 (1980), followed by a DEAE Sepharose purification step. That is, human placenta prewashed successively with water, 50 mM Tris-HCl buffer solution (pH 7.5) containing 1.0M NaCl, and 0.5M acetic acid, was homogenized and suspended in 0.5M acetic acid, and then pepsin treatment was performed at 4° C. for 24 hours.

This mixture is centrifuged, the supernatant is collected and the NaCl concentration is adjusted to 1.0M, after which the solution is stirred for 24 hours and centrifuged, the supernatant is collected and the NaCl concentration is further adjusted to 1.8M, and after further stirring for 24 hours and centrifugation a precipitate is collected. This precipitate was dissolved in 50 mM Tris-HCl buffer solution (pM 7.5) containing 1.0M NaCl, the pH was adjusted to 7.5 with 1.0M sodium hydroxide for dissolution, after the insoluble material was removed by centrifugation the NaCl concentration was raised to 2.0M, the solution was stirred for 24 hours and centrifuged to collect a precipitate which was then dissolved in 0.1M acetic acid to a concentration of 1.0 mg/ml. Solid NaCl was added to 0.7M and the solution was stirred for 24 hours and centrifuged, then the supernatant was collected, and the NaCl concentration was increased to 1.8M. The solution was further stirred for 24 hours and centrifuged, the precipitate was collected and dissolved in 0.1M acetic acid to a concentration of 0.1 mg/ml, the NaCl concentration was adjusted to 0.7M, the solution was stirred for 24 hours and centrifuged, and then the precipitate was collected and purified with DEAE SEPHAROSE (DEAE agarose) to obtain human type IV collagen.

(b) Preparation of human type IV collagen-specific antibody

The human type IV collagen prepared in (a) above was mixed with Freund's complete adjuvant (product of DIFCO Co.) and subcutaneously injected into rabbits at 1.0 mg per rabbit for immunization. Booster shots were given at 4 weeks after the initial immunization by the same method, and blood was taken while monitoring the antibody titer.

Blood was first taken when the antibody titer began to increase, and blood was taken every week thereafter for a total period over one year while booster shots were given every 3 months. The antibody was purified from the serum by affinity chromatography on a column of immobilized human type IV collagen and then it was further purified on a protein A-Sepharose CL-4B column to obtain specific anti-human type IV collagen antibody (polyclonal antibody).

TABLE 1

| Reactivity of polyclonal antibody | | | | | |
|---|---|---|---|---|---|
| | Reactivity absorbance at 415 nm Human collagen | | | | |
| | (−) | I | III | IV | V |
| Polyclonal antibody | 0.012 | 0.016 | 0.014 | 0.892 | 0.019 |

Example 2

Production of anti-human type IV collagen monoclonal antibody (a) Preparation of mouse spleen cells immunized with human type IV collagen Human type IV collagen prepared from human placenta following the method of Sage, et al. described in J. Biol. Chem., 254, 9893–9900 (1980), followed by a DEAE Sepharose purification step was mixed with Freund's complete adjuvant (product of DIFCO Co.), and intraperitoneally injected into BALB/c mice of 8 weeks old at 100 μg per mouse for immunization. Booster shots were given twice at 3 week intervals after the initial immunization by the same method, and on the 3rd day after the final immunization the spleens were dissected and the spleen cells were fused with myeloma cells in the following manner.

(b) Cell fusion

Cell fusion of $2 \times 10^7$ cells of the mouse myeloma cell line P3-X63-Ag8-U1 (P3U1) and $1 \times 10^8$ spleen cells was performed according to the method of Iwasaki, et al. (Monoclonal Antibodies, Kodansha, 1983), in the presence of 50% polyethylene glycol 1500 (product of Boehringer Mannheim Biochemicals).

The fused cells were suspended in ERDF medium (product of Kyokuto Pharmaceuticals Co.) containing 15% fetal calf serum (product of M. A. Bioproducts Co.), and cultured on a 96-well plate (product of Falcon Co.). On day 2 of the culture, the medium was changed to ERDF medium containing 100 μM hypoxanthine, 0.4 μM aminopterin, 16 μM thymidine and 15% fetal calf serum (hereunder, "HAT medium"), and HAT medium was further added after 3 days.

After one week the HAT medium was replaced with the medium lacking aminopterin (hereunder, "HT medium"), and HT medium was replaced every 3-4 days thereafter. At about 2 weeks after the cell fusion, when the growth of the fused cells could be visually confirmed, the anti-human type IV collagen antibody titer in the culture supernatant was measured by the enzyme immunoassay method described below, and cells producing the anti-human type IV collagen antibody were screened.

(c) Screening of anti-human type IV collagen antibody-producing cells by enzyme immunoaseay method Fifty μl of 10 μg/ml human type IV collagen was added to each well of an immunoplate (Maxisorp, product of Nunc Co.) for coating overnight at 4° C., and after washing once with phosphate-buffered saline-0.05% Tween 20 (hereunder, "PBS-Tween"), blocking was performed with PBS-Tween containing 0.1% bovine serum albumin.

50 μl of the hybridoma culture supernatant obtained in (b) above, was added to each of the treated wells and the plate was incubated at 37° C. for one hour. After washing with PBS-Tween, peroxidase-labelled goat anti-mouse IgG antibody was added as the second antibody, and reaction mixture was incubated at 37° C. for one hour. To each of the washed wells there was added 100 μl of a peroxidase substrate solution, i.e. 0.3 mg/ml 2,2'-azino-bis(3-ethylbenzthiazoline-6-sulfonic acid) diammonium salt—0.003% hydrogen peroxide—0.1M phosphate/citrate buffer solution (pH 4.0), and the wells wee incubated for 30 minutes. After stopping the reaction by the addition of 100 μl of 1.5% oxalic acid, the absorbance at 415 nm was measured with a microplate reader (MPR-A4, product of TOSOH CORP.).

(d) Cloning of hybridoma producing anti-human type IV collagen antibody

The cells in the wells confirmed to be producing anti-human type IV collagen antibody through screening by the enzyme immunoassay method in (c) above were then cloned by the limiting dilution method as follows. The cells were dispensed into a 96-well plate at cell counts of 3, 1 and 0.3 per well, and were cultured in HT medium.

After 10 to 14 days, when growth of the cells could be visually confirmed, the anti-human type IV collagen antibody titer in each of the culture supernatants was determined by enzyme immunoassay in the same manner as in (c) above. The cells in the wells which were found producing anti-human type IV collagen antibody were repeatedly re-cloned, until production of anti-human type IV collagen antibody was finally confirmed in all of the wells. Thus, there were obtained 2 anti-human type IV collagen antibody-producing hybridoma lines.

(e) Production of anti-human type IV collagen monoclonal antibody

For production of monoclonal antibodies by the two hybridoma lines mentioned above, each of the hybridoma lines was cultured in the abdominal cavity of BALB/c mice which had been previously administered pristane (2,6,10,14-tetramethylpentadecane) intraperitoneally at 0.5 ml per mouse. The administration of $5 \times 10^6$ hybridoma cells into mouse intraperitoneal cavity resulted in the antibody production of 1–10 mg/ml in the ascites fluid by the 10th to 14th day of post-injection.

(f) Purification of monoclonal antibodies

The monoclonal antibodies in the ascites fluid obtained in (e) above were diluted to two-fold with 1.5M glycine-Na buffer (pH 8.5) containing 3.0M NaCl, and applied to a protein A-Sepharose CL-4B column which had been equilibrated with 1.5M glycine-Na buffer (pH 8.5) containing 3.0M NaCl. After washing the column with the equilibration buffer, the monoclonal antibody bound on the column was eluted with 0.1M citric acid-Na buffer solution (pH 4.0).

The two monoclonal antibodies thus purified were characterized for specificity with human collagen type I, III, IV and V, by enzyme immunoassay as described in (c) above. The results were shown in Table 2.

TABLE 2

Specificity of monoclonal antibodies

| Monoclonal antibody | Reactivity Absorbance at 415 nm Human collagen | | | | |
|---|---|---|---|---|---|
| | (−) | I | III | IV | V |
| 67 | 0.024 | 0.027 | 0.030 | 1.729 | 0.034 |
| 238 | 0.025 | 0.029 | 0.041 | 1.244 | 0.026 |

The hybridomas producing monoclonal antibodies 67 and 238 in Table 2 were named COL IV-67 and COL IV-238, respectively. Both of which had been deposited at the National Institute of Bioscience and Human Technology on Sep. 27, 1994 as FERM P-14561 and FERM P-14560, respectively, and transferred to an international deposition under the Budapest treaty as FERM BP-5240 and FERM BP-5239, respectively on Sep. 25, 1995. Hereunder, the monoclonal antibody produced by the hybridoma COL IV-67 will be referred to simply as monoclonal antibody 67, and the monoclonal antibody produced by the hybridoma COL IV-238 will be referred to simply as monoclonal antibody 238.

The results obtained by SDS-polyacrylamide gel electrophoresis under reduced and non-reduced conditions followed by immunoblotting, showed that monoclonal antibody 67 has the following properties:

(1) It is raised against the pepsin-solubilized human type IV collagen;
(2) It binds to the 7S domain of human type IV collagen but not to other domains;
(3) It does not bind to human type I, type III and type V collagen;
(4) When analyzed by SDS-polyacrylamide gel electrophoresis under reduced condition, the molecular weight of the heavy (H) chains is about 51,000 and the molecular weight of the light (L) chain is about 28,000; and (5) It is IgG1κ subtype, and that monoclonal antibody 238 has the following properties:
   (1) It is raised against the pepsin-solubilized human type IV collagen;
   (2) It binds to domains other than the 7S domain of human type IV collagen but does not bind to the 7S domain;
   (3) It does not bind to human type I, type III and type V collagen;
   (4) When analyzed by SDS-polyacrylamide gel electrophoresis under reduced condition, the molecular weight of the heavy (H) chain is about 50,000 and the molecular weight of the light (L) chain is about 27,000; and
   (5) It is IgG2κ subtype.

Example 3

Antigenic sites of monoclonal antibodies
(a) Preparation of human type IV collagen 7S long form The 7S long form of human type IV collagen was prepared from human placenta following the method of Risteli, et al. described in Eur. J. Biochem., 108, 239–250 (1980).
(b) Reactivity of monoclonal antibodies against human type IV collagen and human type IV collagen 7S long form To each well of an immunoplate there was added 50 μl of 10 μg/ml human type IV collagen or the human type IV collagen 7S long form (hereunder, "7S domain") for coating overnight at 40° C., and after washing once with phosphate-buffered saline-0.05% Tween 20 (hereunder, "PBS-Tween"), blocking was performed with PBS-Tween containing 0.1% bovine serum albumin, to prepare plates containing each of the antigens in solid phase.

To each well of the plates coated with human collagen type IV and its 7S domain independently, there was added 50 μl of respective monoclonal antibody and rabbit polyclonal antibody at concentrations of 0.10 or 0.50 μg/ml, and reaction was performed at 37° C. for 2 hours. After washing the wells with PBS-Tween, peroxidase-labelled anti-mouse IgG antibody was added to each well to which the monoclonal antibody had been added and peroxidase-labelled anti-rabbit IgG antibody was added to each well to which the specific antibody had been added, and reaction was performed at 37° C. for one hour. After washing each well with PBS-Tween, 100 μl of 0.3 mg/ml 2,2'-azino-bis(3-ethylbenzthiazoline-6-sulfonic acid) diammonium salt—0.003% hydrogen peroxide—0.1M phosphate/citrate buffer (pH 4.0) was added, and the reaction was performed for 30 minutes. The reaction was stopped by the addition of 100 μl of 1.5% oxalic acid and absorbance at 415 nm was measured with a microplate reader (MPR-A4, product of TOSOH CORP.). The results the measurement are shown in FIGS. 1-a and 1-b.

Although both the monoclonal and polyclonal antibodies recognize human type IV collagen (FIG. 1-a), only the monoclonal antibody 67 and the specific antibody recognize the 7S domain (FIG. 1-b).
(c) The sites of human type IV collagen recognized by monoclonal antibodies To each well of an immunoplate there was added 200 μl of a 5 μg/ml solution of monoclonal antibody 67 or 238 for coating overnight at 4° C. After washing the wells once with PBS-Tween, blocking was performed with PBS-Tween containing 0.1% bovine serum albumin, to prepare two plates containing each of the monoclonal antibodies in solid phase.

To each well of the plates there was added 100 μl of a monoclonal antibody solution containing either monoclonal antibody 67 or monoclonal antibody 238 to the final antibody concentrations of 0, 0.37, 1.10, 3.35 and 10.0 μg, after which 100 μl of a 200 ng/ml human type IV collagen solution was added to all of the wells and the plates were incubated at 37° C. for 2 hours. After washing with PBS-Tween, the above-mentioned peroxidase-labelled polyclonal antibody was added, and the plates were incubated at 37° C. for one hour.

After washing with PBS-Tween, 200 μl of 0.3 mg/ml 2,2'-azino-bis(3-ethylbenzthiazoline-6-sulfonic acid) diammonium salt—0.003% hydrogen peroxide—0.1M phosphate/citrate buffer (pM 4.0) was added. After incubation for 30 minutes, 100 μl of a 2.25% oxalic acid solution was added to stop the reaction, and then the absorbance at 415 nm was measured in the same manner as in (b), giving the results shown in FIGS. 2 and 3.

Figure 2:
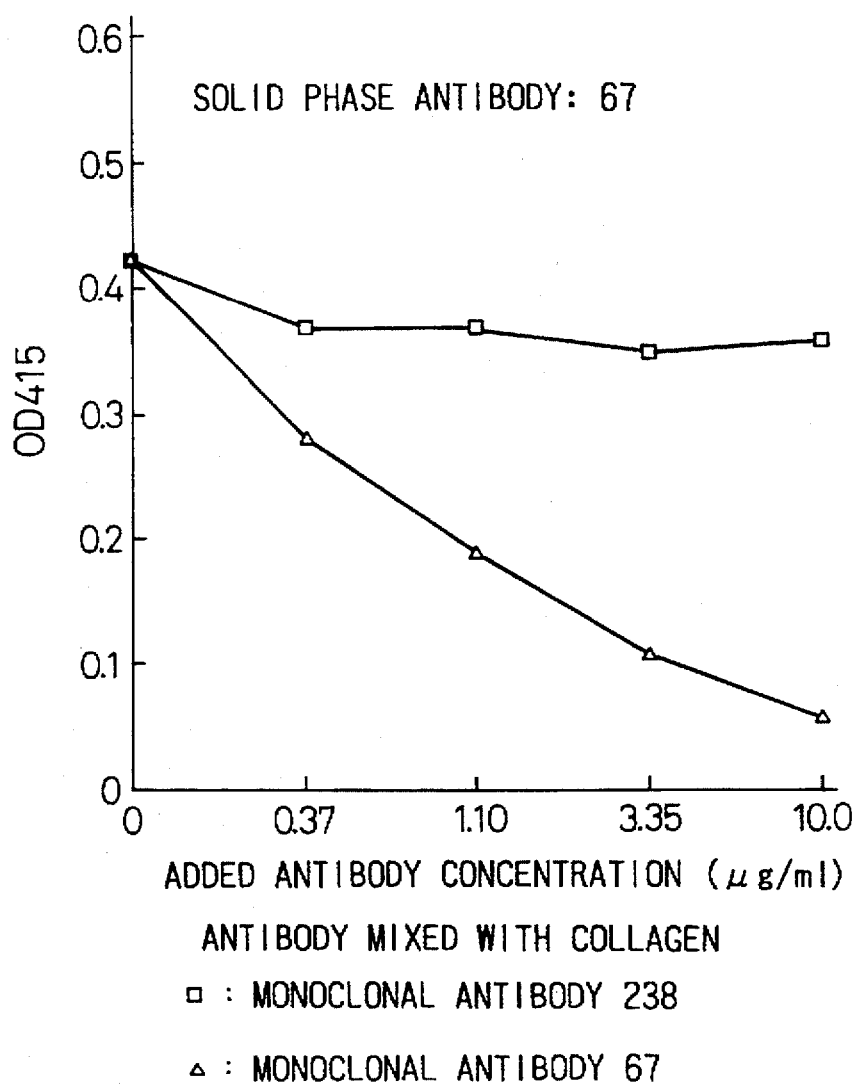
FIG. 2 is a graph showing the results of analyzing the identities of the binding sites of the monoclonal antibodies 238 and 67 of the present invention on the human type IV collagen molecule.
Figure 3:
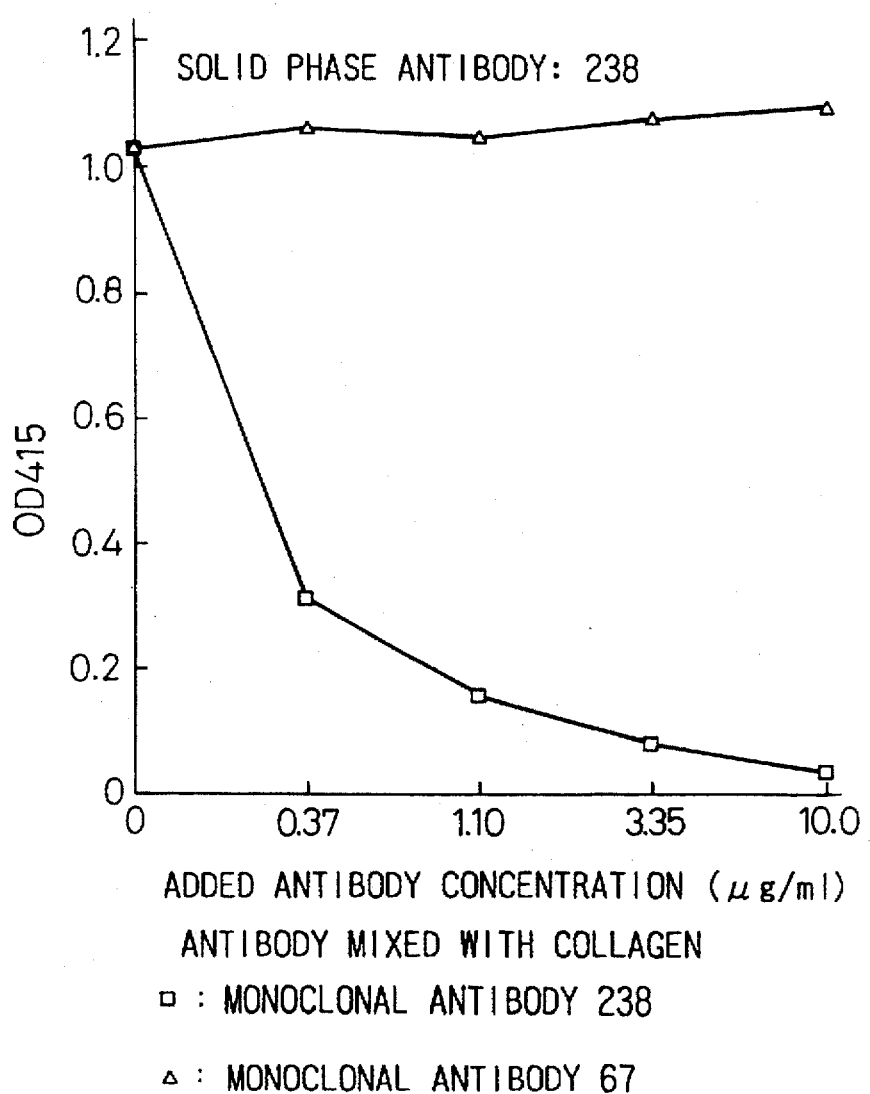
FIG. 3 is a graph showing the results of analyzing the identities of the binding sates of the monoclonal antibodies 238 and 67 of the present invention on the human type IV collagen molecule.

Based on FIGS. 2 and 3 it is concluded that monoclonal antibody 67 and monoclonal antibody 238 recognize different sites on human type IV collagen; that is, considering the results in Table 2 and FIGS. 1-a and 1-b together monoclonal antibody 67 recognizes the 7S domain of human type IV collagen and monoclonal antibody 238 recognizes a site other than the 7S domain.

Example 4

Making a calibration curve 2 ml of a boric acid buffered solution (50 mM boric acid, 0.15M Nacl, pH 8.5) containing either monoclonal antibody 67 or 238 at the concentration of 62.5 μg/ml, was added to 1,000 polystyrene beads with an average diameter of 1.2 mm. The mixture was gently stirred for overnight at room temperature to immobilize the antibody on the surface of the beads. After washing with Tris-HCl buffer solution (pH 8.0), Tris-HCl buffer solution (pH 8.0) containing 0.5% bovine serum albumin (BSA), was added to the beads, and the mixture was heated at 53° C. for 3 hours for blocking treatment.

After washing with PBS, 12 of the beads prepared in this manner were used in the following experiment.

To prepare alkaline phosphatase (ALP) labelled polyclonal antibody, 6 mg of the polyclonal antibody prepared in Example 1 and 6 mg of commercially available bovine intestinal ALP (product of Biozyme) were used, and these were connected by S—S bonding and subjected to gel filtration (column: G3000SW, product of TOSOH CORP.; elution: 59 mM phosphate buffer solution (pH 7) containing 150 mM NaCl) to isolate the enzyme-antibody complex (Ishikawa, E. et al., Enzyme Immunoassays, 3rd Edition, Igaku Shoin, p. 117-). The ALP-labeled polyclonal antibody conjugate was diluted to have an absorbance (ABS) of 0.0005 to 0.005 at 280 nm with a 0.1M Tris-HCl buffer solution (pH 7.5) containing 10% BSA, 1 mM $MgCl_2$ and 0.1 mM $ZnCl_2$.

Standard collagen solutions were prepared in the following manner. First, human type IV collagen was prepared according to the method described in Example 1(a). The protein concentration was measured according to Lowry et. al. and found to be 590 μg/ml. The diluting medium free from type IV collagen was prepared in the following manner. That is, a polyclonal antibody against the human type IV collagen from Example 1 was immobilized on CNBr-activated CL-4B to prepare a column through which normal human blood serum was passed to adsorb and remove the human type IV collagen and fragments thereof from the blood serum, and thus human blood serum free of human type IV collagen was obtained.

The above-mentioned collagen was diluted with this serum, to prepare collagen standard solutions containing 5–640 ng/ml of human type IV collagen. Serum containing no collagen was used as a control sample.

Immunoassay was performed using the monoclonal antibody-immobilized beads, the ALP enzyme-labelled polyclonal antibody and the human type IV collagen standard solution. The assay was performed with a commercially available fully automated immuno analyzer (AIA-1200, product of TOSOH CORP.).

Twelve of the monoclonal antibody-immobilized beads, 100 μl of the labelled polyclonal antibody (0.002 ABS when the immobilized antibody was antibody 67, and 0.0005 ABS when the immobilized antibody was antibody 238) and a specimen (type IV collagen standard solution) (50 μl when the immobilized antibody was antibody 67, and 20 μl when the immobilized antibody was antibody 238) were mixed and allowed to react at 37° C. for 40 minutes, after which the beads were separated from the reaction mixture.

After 220 μl of a substrate solution (pH 10) containing the ALP enzyme substrate 4-methylumbelliferone phosphate (4 MUP) at a concentration of 0.26 mg/ml was added to the washed beads, the reaction rate in terms of 4-methylumbelliferone (4 MU) increase was measured at an excitation wavelength of 362 nm and a measuring wavelength of 447 nm. 4 MUP is converted to 4 MU by the action of the enzyme ALP.

Figure 4:
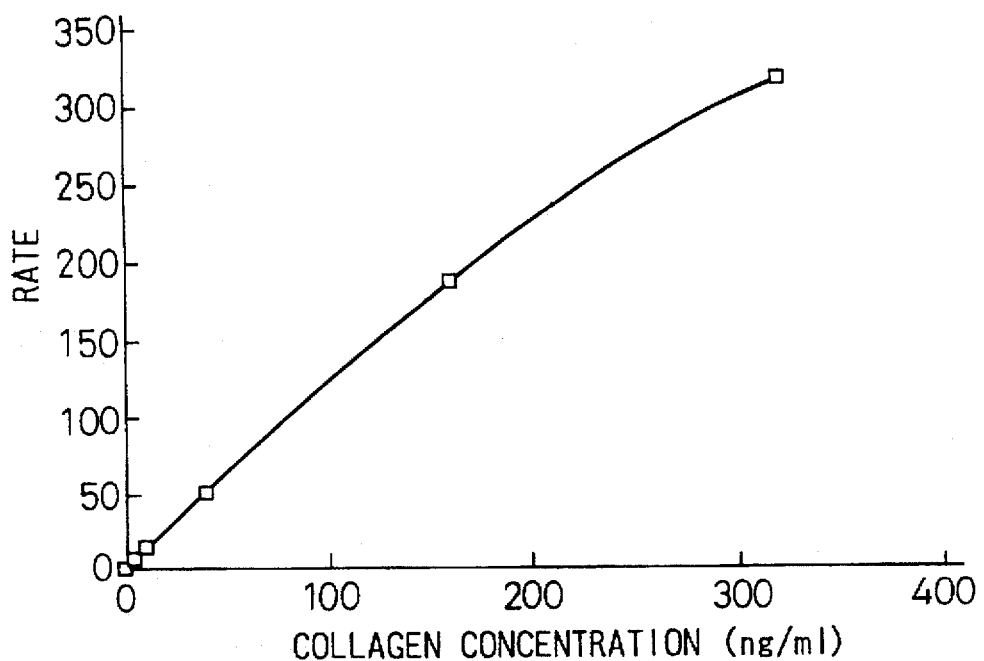
FIG. 4 is an example of a calibration curve for an assay of human type IV collagen using monoclonal antibody 67 as the immobilized antibody (primary antibody).
Figure 5:
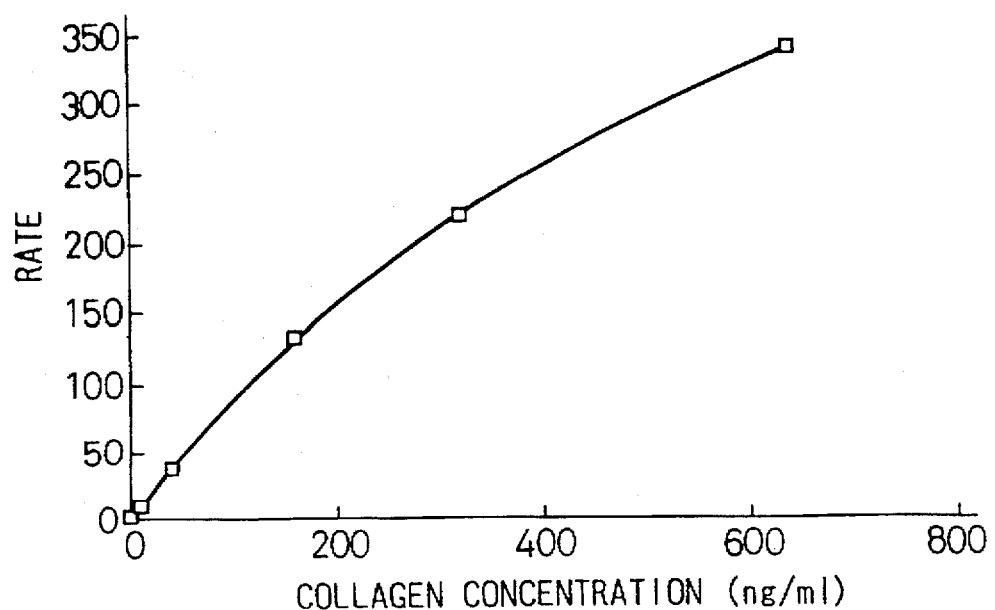
FIG. 5 is an example of a calibration curve for an assay of human type IV collagen using monoclonal antibody 238 as the immobilized antibody (primary antibody).

The results of using monoclonal antibody 67 as the immobilized antibody are shown in Table 3 and FIG. 4, and the results of using monoclonal antibody 238 as the immobilized antibody are shown in Table 4 and FIG. 5.

TABLE 3

| | Collagen conc. | Average | S.D. | CV (%) | Rate-1 | Rate-2 |
|---|---|---|---|---|---|---|
| 1 | 0 | 0.466 | 0.108 | 23.24 | 0.542 | 0.389 |
| 2 | 5 | 7.238 | 0.086 | 1.18 | 7.298 | 7.177 |
| 3 | 10 | 14.652 | 0.146 | 1.00 | 14.548 | 14.755 |
| 4 | 40 | 50.159 | 0.076 | 0.15 | 50.212 | 50.105 |
| 5 | 160 | 187.425 | 4.805 | 2.56 | 184.027 | 190.823 |
| 6 | 320 | 316.944 | 24.452 | 7.72 | 299.653 | 334.234 |

TABLE 4

| | Collagen conc. | Average | S.D. | CV (%) | Rate-1 | Rate-2 |
|---|---|---|---|---|---|---|
| 1 | 0 | 0.078 | 0.020 | 25.38 | 0.092 | 0.064 |
| 2 | 10 | 9.304 | 0.078 | 0.94 | 9.359 | 9.248 |
| 3 | 40 | 37.604 | 0.707 | 1.88 | 37.104 | 38.104 |
| 4 | 160 | 133.246 | 11.463 | 8.60 | 125.14 | 141.351 |
| 5 | 320 | 220.227 | 9.055 | 4.11 | 226.63 | 213.824 |
| 6 | 640 | 340.402 | 23.689 | 6.96 | 357.153 | 323.651 |

In these tables, "Collagen conc." is the concentration of standard human type IV collagen in ng/ml, "S.D." is the standard deviation of duplicate measurements, "CV %" is the coefficient of variation, and "Rate-1" and "Rate-2" are two measurements of the rate of increase of 4 MU.

Example 5

Measurement of samples

Ten human serum samples (A–J) were measured in duplicate by each of the methods of the present invention (using monoclonal antibody 67 as the immobilized antibody and using monoclonal antibody 238 as the immobilized antibody), and averages, standard deviations and CV percentages were calculated based on the results.

Table 5 shows the results obtained based on the calibration curve in FIG. 4 which is constructed using the data of Table 3, using monoclonal antibody 67 as the immobilized antibody in the method of the present invention, and Table 6 shows the results obtained based the calibration curve in FIG. 5 which is constructed using the data of Table 4, using monoclonal antibody 238 as the immobilized antibody in the method of the present invention. "Conc.-1" and "Conc.-2" in the tables are the results of two measurements.

TABLE 5

| Sample | Average | S.D. | CV (%) | Conc.-1 (ng/ml) | Conc.-2 (ng/ml) |
|---|---|---|---|---|---|
| A | 96.576 | 0.659 | 0.66 | 97.04 | 96.11 |
| B | 9.849 | 1.513 | 15.36 | 10.92 | 8.78 |
| C | 53.061 | 2.067 | 3.89 | 54.52 | 51.60 |
| D | 22.743 | 0.613 | 2.69 | 23.18 | 22.31 |
| E | 16.553 | 0.389 | 2.35 | 16.83 | 16.28 |
| F | 127.005 | 21.095 | 16.61 | 141.92 | 112.09 |
| G | 16.375 | 0.332 | 2.03 | 16.61 | 16.14 |
| H | 18.242 | 0.461 | 2.53 | 18.57 | 17.92 |
| I | 10.734 | 0.663 | 6.36 | 10.25 | 11.22 |
| J | 8.555 | 0.309 | 3.61 | 8.77 | 8.34 |

TABLE 6

| Sample | Average | S.D. | CV (%) | Conc.-1 (ng/ml) | Conc.-2 (ng/ml) |
|---|---|---|---|---|---|
| A | 621.590 | 53.196 | 8.56 | 583.97 | 659.21 |
| B | 102.049 | 2.264 | 2.22 | 103.65 | 100.45 |
| C | 169.297 | 1.894 | 1.12 | 170.64 | 167.96 |
| D | 73.850 | 3.305 | 4.47 | 71.51 | 76.19 |
| E | 158.032 | 4.961 | 3.14 | 161.54 | 154.52 |
| F | 430.872 | 79.884 | 18.54 | 487.36 | 374.39 |
| G | 87.691 | 2.740 | 3.12 | 85.75 | 89.63 |
| H | 205.676 | 10.781 | 5.24 | 198.05 | 213.30 |
| I | 108.614 | 2.820 | 2.60 | 110.61 | 106.62 |
| J | 54.632 | 1.952 | 3.57 | 56.01 | 53.25 |

Example 6

Blood serum was taken from 48 patients diagnosed with liver cirrhosis who were conclusively diagnosed so based on examinations on GPT, GOT, etc. and/or on inquiry by a physician, and the serum was assayed for type IV collagen for determining positivity according to the method of the present invention.

Measurements were also made using two commercially available type IV collagen assay kits, "Type IV Collagen-7S kit" (product of Nihon DPC Corporation, KK.) (hereunder, "kit 1") and "Panassay IV-C" (purchased from Daiichi Chemicals, KK., produced by Fuji Yakuhin Kogyo, KK.) (hereunder, "kit 2"), and the results were compared with those obtained by the present invention.

For determining positivity and negativity from the results of measurement by the method of the present invention, the [average+2×S.D.] value determined with sera from 33 healthy volunteers (shown in Table 7) were used as the cutoff value, against which higher values were defined as positive and lower values were defined as negative. For determination judgment with kits 1 and 2, the cutoff was performed with the values indicated in the instructions of each kit, i.e. 5 ng/ml for kit 1 and 140 ng/ml for kit 2.

TABLE 7

| Sample | Immobilized antibody 67 | Immobilized antibody 238 |
|---|---|---|
| 1 | 6.424 | 67.197 |
| 2 | 6.769 | 64.037 |
| 3 | 6.864 | 82.39 |
| 4 | 7.828 | 64.481 |
| 5 | 5.396 | 73.849 |
| 6 | 7.411 | 73.32 |
| 7 | 5.561 | 85.494 |
| 8 | 4.122 | 70.833 |
| 9 | 4.663 | 73.386 |
| 10 | 6.294 | 60.649 |
| 11 | 4.461 | 75.455 |
| 12 | 4.594 | 79.916 |
| 13 | 4.495 | 72.946 |
| 14 | 4.468 | 55.701 |
| 15 | 4.805 | 45.547 |
| 16 | 6.58 | 89.769 |
| 17 | 6.125 | 70.279 |
| 18 | 5.515 | 65.086 |
| 19 | 6.744 | 81.65 |
| 20 | 5.517 | 66.671 |
| 21 | 4.542 | 75.863 |
| 22 | 7.254 | 49.168 |
| 23 | 4.482 | 49.495 |
| 24 | 4.17 | 61.094 |
| 25 | 4.629 | 61.345 |
| 26 | 9.937 | 54.674 |
| 27 | 8.586 | 79.371 |
| 28 | 6.558 | 67.543 |
| 29 | 2.765 | 36.309 |
| 30 | 5.903 | 68.667 |
| 31 | 4.655 | 62.458 |
| 32 | 6.015 | 78.753 |
| 33 | 6.777 | 70.84 |
| Average | 5.79 | 67.70 |
| S.D. | 1.48 | 11.94 |
| Average + 2 × S.D. | 8.74 | 91.59 |

The measurement by the present invention was made as described in Example 4 and for kits 1 and 2 the measurement was made according to the instructions.

The results are shown in Tables 8 and 9. Blank areas in the column indicate cases where no measurement could be made due to insufficient sample.

TABLE 8

| Patient | Commercial kit | | Method of the invention | |
|---|---|---|---|---|
| | Kit 1 | Kit 2 | Immobilized antibody 67 | Immobilized antibody 238 |
| 1 | 12.22 | 205 | 44.696 | 177.981 |
| 2 | 27.797 | 870 | 82.893 | 234.763 |
| 3 | 17.131 | 505 | 83.373 | 251.132 |
| 4 | 12.22 | 235 | 53.444 | 219.085 |
| 5 | 15.114 | 280 | 58.21 | 301.588 |
| 6 | 12.913 | 205 | 45.587 | 166.048 |
| 7 | 6.285 | 112 | 16.382 | 112.165 |
| 8 | 10.387 | | 48.79 | 114.605 |
| 9 | 8.483 | 148 | 26.606 | 164.461 |
| 10 | 13.739 | | 40.672 | 196.066 |
| 11 | 19.407 | | 90.556 | 267.021 |
| 12 | 20.227 | 980 | 111.825 | 486.115 |
| 13 | | | | |
| 14 | 5.393 | 118 | 7.016 | 78.59 |
| 15 | 12.624 | 185 | 104.421 | 226.907 |
| 16 | 8.703 | 148 | 21.331 | 114.231 |
| 17 | 18.365 | 240 | 100.008 | 180.025 |
| 18 | 13.344 | 192 | 58.263 | 165.545 |
| 19 | 3.935 | | 10.065 | 143.1 |
| 20 | 9.588 | 125 | 22.363 | 133.061 |
| 21 | 10.401 | | 31.665 | 99.153 |
| 22 | 13.231 | 305 | 56.892 | 224.841 |
| 23 | 12.136 | 240 | 36.034 | 208.711 |
| 24 | 11.821 | 220 | 43.348 | 158.578 |
| 25 | 9.219 | 175 | 27.931 | 217.29 |
| 26 | 14.655 | 170 | 48.341 | 164.446 |
| 27 | 20.053 | 155 | 52.167 | 100.644 |
| 28 | 8.451 | 133 | 29.931 | 140.6 |
| 29 | 11.202 | | 44.974 | 114.196 |
| 30 | 9.851 | 122 | 40.11 | 149.389 |

TABLE 9

| Patient | Commercial kit | | Method of the invention | |
|---|---|---|---|---|
| | Kit 1 | Kit 2 | Immobilized antibody 67 | Immobilized antibody 238 |
| 31 | 8.925 | 88 | 25.682 | 75.848 |
| 32 | 13.175 | 215 | 51.913 | 139.804 |
| 33 | 12.509 | | 44.36 | 87.486 |
| 34 | 8.476 | 149 | 28.378 | 59.139 |
| 35 | 7.86 | 208 | 12.723 | 136.492 |
| 36 | 9.924 | | 21.555 | 133.874 |
| 37 | 15.617 | | 55.75 | 505.337 |
| 38 | 9.844 | 198 | 57.997 | 166.675 |
| 39 | 4.978 | | 20.991 | 97.594 |
| 40 | 27.044 | 630 | 119.286 | 328.328 |
| 41 | 8.04 | 145 | 26.56 | 129.211 |
| 42 | 9.516 | 160 | 21.483 | 131.673 |
| 43 | 9.91 | 150 | 27.04 | 98.02 |
| 44 | 5.768 | 110 | 16.084 | 77.771 |
| 45 | 8.502 | | 17.298 | 111.341 |
| 46 | 10.415 | 147 | 31.887 | 109.976 |
| 47 | 14.288 | 370 | 62.585 | 182.646 |
| 48 | 7.268 | 170 | 17.716 | 160.668 |
| 49 | 10.793 | 128 | 53.49 | 92.4 |
| Average | 11.91 | 241.51 | 44.81 | 169.47 |
| S.D. | 5.00 | 197.35 | 27.35 | 91.01 |
| Cutoff | 5.0 | 140 | 8.74 | 91.59 |
| Positivity | 95.83 (46/48) | 78.38 (29/37) | 97.92 (47/48) | 89.58 (44/48) |

According to the results in Table 7–9, the assays by the present invention with serum samples from liver cirrhosis patients exhibited positivity of about 90% or even higher, and nearly 100%, whereas with the commercial kit 2 did not accurately reflect the pathological condition of the patients, since antibodies were all monoclonal and detectable type IV collagen fragments were limited.

Example 7

Forty patients diagnosed with hepatitis who had undergone liver biopsy were divided into groups based on the results of the liver biopsy (HAI score category 4, Knodell, et al., Hepatology, vol. 1, 1981, p. 431–435), into a first group (patients with no fibrosis and patients with mild fibrous portal expansion: 21, group 0 and group 1 in terms of HAI score) and a second group (patients with portal bridging fibrosis and patients with liver cirrhosis: 19, group 3 and group 4 in terms of score).

Sera were taken from patients of each group, and type IV collagen concentrations were measured by the method of the present invention and using kits 1 and 2 described in Example 5. The measurement was performed according to Example 4 in the case for the present invention, and as indicated in the instructions for commercially kits. The results for group 1 sera are shown in Table 10, and group 2 in Table 11.

TABLE 10

| Commercial kit | | Present invention | | HAI | Pathological |
|---|---|---|---|---|---|
| Kit 1 | Kit 2 | Immobilized antibody 67 | Immobilized antibody 238 | score | findings |
| 9.851 | 122 | 40.11 | 149.389 | 1 | CAH2A |
| 4.544 | 56 | 4.983 | 54.76 | 1 | CAH2A |
| 3.742 | 82 | 6.47 | 70.553 | 1 | CAH2A |
| 5.536 | 132 | 7.35 | 88.018 | 0 | |
| 12.338 | 152 | 23.109 | 98.675 | 1 | CAH2A |
| 5.409 | | 9.247 | 70.345 | 0 | |
| 4.525 | 84 | 6.997 | 68.605 | 1 | CAH2A |
| 6.378 | 100 | 11.735 | 126.325 | 1 | CAH2A |
| 6.046 | 143 | 11.221 | 121.599 | 1 | CAH2A |
| 4.194 | 69 | 7.468 | 54.266 | 1 | CAH2A |
| 3.569 | 108 | 10.041 | 127.469 | 1 | CAH2A |
| 5.631 | 51 | 7.498 | 74.012 | 1 | CAH2A |
| 3.392 | 38 | 7.346 | 72.533 | 1 | CAH2A |
| 4.637 | 75 | 8.088 | 69.719 | 1 | CAH2A |
| 5.464 | 97 | 13.516 | 71.783 | 1 | CAH2A |
| 4.287 | 83 | 9.423 | 89.442 | 1 | CAH2A |
| 4.39 | 78 | 9.529 | 74.015 | 1 | CAH2A |
| 16.228 | 260 | 35.051 | 143.787 | 0 | CIH |
| 3.705 | 71 | 5.825 | 46.723 | 1 | CAH2A |
| 8.515 | | 28.692 | 150.536 | 1 | CAH2A |
| 3.406 | 46 | 8.787 | 54.892 | 1 | CAH2A |

CAH: Chronic active hepatitis
CIH: Chronic inactive hepatitis
Blank: No abnormal pathological findings

TABLE 11

| Commercial kit | | Present invention | | HAI | Pathological |
|---|---|---|---|---|---|
| Kit 1 | Kit 2 | Immobilized antibody 67 | Immobilized antibody 238 | score | findings |
| 12.913 | 205 | 45.587 | 166.048 | 4 | LC |
| 6.285 | 112 | 16.382 | 112.165 | 3 | CAH2B |
| 13.738 | | 40.672 | 196.066 | 4 | LC(+HCC) |
| 9.588 | 125 | 22.363 | 133.061 | 3 | CAH2A |
| 13.231 | 305 | 56.892 | 224.841 | 3 | CAH2B |
| 8.476 | 149 | 28.378 | 59.139 | 4 | LC |
| 4.978 | | 20.991 | 97.594 | 3 | CAH2B |
| 27.044 | 630 | 119.286 | 328.328 | 4 | LC |
| 8.473 | | 33.947 | 179.309 | 3 | CAH2B |
| 6.13 | | 16.307 | 120.62 | 3 | CAH2B |
| 4.381 | 73 | 12.125 | 101.067 | 3 | CAH2B |
| 6.257 | 115 | 14.477 | 58.84 | 3 | CAH2B |
| 5.554 | 87 | 9.579 | 46.989 | 3 | CAH2B |
| 6.726 | 270 | 20.918 | 153.125 | 3 | CAH2B |
| 6.892 | | 14.923 | 115.767 | 3 | CAH2B |
| 13.307 | 210 | 41.127 | 134.556 | 4 | LC |
| 6.52 | | 9.013 | 101.481 | 3 | CAH2B |
| 6.34 | 102 | 13.664 | 82.033 | 3 | CAH2B |
| 7.101 | 102 | 24.6 | 82.77 | 3 | CAH2B |

LC: Liver cirrhosis
CAH: Chronic active hepatitis
HCC: Hepatocellular carcinoma

The results for groups 1 and 2 were subjected to a t-test with significance level of 5%, and analyzed to determine whether there was a significant difference between the two groups. For the statistic test it was assumed that there was no significant difference between the measurement results of the two groups. The results are shown in Tables 12–15. Table 12 shows the results obtained from the method of the present invention using monoclonal antibody 67 as the immobilized antibody, Table 13 shows the results obtained from the method of the present invention using monoclonal antibody 238 as the immobilized antibody, Table 14 shows the results using the commercial kit 1 and Table 15 shows the results using the commercial kit 2.

TABLE 12

| | Group 2 | Group 1 |
|---|---|---|
| Average | 29.538474 | 12.975524 |
| Variance | 651.45536 | 99.170191 |
| Number of samples | 19 | 21 |
| Pooled variance | 3.5 | |
| Degrees of freedom | 22.908647 | |
| t | 2.6518711 | |
| P (T <= t)   1-sided | 0.0072827 | |
| t boundary value  1-sided | 1.7171442 | |
| P (T <= t)   2-sided | 0.0145655 | |
| t boundary value  2-sided | 2.0738753 | |

TABLE 13

| | Group 2 | Group 1 |
|---|---|---|
| Average | 131.25258 | 89.40219 |
| Variance | 4543.1142 | 1114.2264 |
| Number of samples | 19 | 21 |
| Pooled variance | 3.5 | |
| Degrees of freedom | 25.734229 | |
| t | 2.4483975 | |
| P (T <= t)   1-sided | 0.0108541 | |
| t boundary value  1-sided | 1.7081402 | |
| P (T <= t)   2-sided | 0.0217083 | |
| t boundary value  2-sided | 2.0595371 | |

TABLE 14

| | Group 2 | Group 1 |
|---|---|---|
| Average | 9.1544211 | 5.9898571 |
| Variance | 27.733801 | 10.590791 |
| Number of samples | 19 | 21 |
| Pooled variance | 3.5 | |
| Degrees of freedom | 29.425513 | |
| t | 2.2581015 | |
| P (T <= t)   1-sided | 0.0158188 | |
| t boundary value  1-sided | 1.6991271 | |
| P (T <= t)   2-sided | 0.0316376 | |
| t boundary value  2-sided | 2.0452308 | |

TABLE 15

| | Group 2 | Group 1 |
|---|---|---|
| Average | 191.15385 | 97.210526 |
| Variance | 22602.808 | 2581.2865 |
| Number of samples | 13 | 19 |
| Pooled variance | 3.5 | |
| Degrees of freedom | 13.892039 | |
| t | 2.1697973 | |
| P (T <= t)   1-sided | 0.0245725 | |
| t boundary value  1-sided | 1.7709317 | |
| P (T <= t)   2-sided | 0.049145 | |
| t boundary value  2-sided | 2.1603682 | |

Since the null hypothesis was that no significant difference existed between the measurement results of both groups, it is shown by the test results that the hypothesis is less established, i.e. a significant difference exists between the measurement results of the two groups, with smaller P values which are the probability of the hypothesis being correct (see Ichihara, K., Statistics for Bioscience, 7th Edition, Nankodo, 1994).

In the t-test with a significance level of 5% performed here, significant differences were found between the measurement results of the two groups by all of the assay methods. However, the method of the present invention gave more highly reliable results of determining human type IV collagen than conventional assay methods presented by the commercial kits 1 and 2. In particular, the P value was lowest when monoclonal antibody 67 was used as the immobilized antibody, showing that the method is the most suitable as an assay method for human type IV collagen.

We claim:

1. A method for immunoassay of human type IV collagen in a sample, comprising contacting a sample with a carrier immobilized monoclonal antibody against human type IV collagen and a labelled polyclonal antibody against human type IV collagen, wherein said monoclonal antibody is produced by a mouse X mouse hybridoma COL IV-67 (FERM BP-5240) and wherein said monoclonal antibody:
   (1) is raised against pepsin-solubilized human type IV collagen, said type IV collagen having been purified at least with DEAE agarose;
   (2) binds to the 7S domain of human type IV collagen but not to other domains;
   (3) does not bind to human type I, type III and type V collagen;
   (4) when analyzed by SDS-polyacrylamide gel electrophoresis under reduced condition, comprises a heavy (H) chain of about 51,000 daltons and a light (L) chain of about 28,000 daltons; and
   (5) is of the IgG1κ subtype; and
   detecting said human type IV collagen in said sample.

2. The method according to claim 1, further comprising steps wherein the carrier with monoclonal antibody against human type IV collagen is immobilized, the labelled polyclonal antibody against human type IV collagen and the sample are mixed together, the labelled polyclonal antibody bound to the carrier through the human type IV collagen in the sample is separated from the unbound labelled polyclonal antibody, and when in cases were an arbitrary amount of the labelled polyclonal antibody has been used, the amount of the label bound to the carrier is measured, whereas if a known amount of the labelled polyclonal antibody has been used, the amount of the label either bound or unbound to the carrier is measured.

3. The method according to claim 2, wherein said carrier is a solid carrier, and the separation of the label which is bound and unbound to the carrier is performed by separating the insoluble solid carrier from the reaction solution.

4. The method according to claim 1, wherein the label of said labelled polyclonal antibody is an enzyme, and said detecting of said human type IV collagen in said sample is made on the basis of the action of said enzyme against a substrate of said enzyme.

5. The method according to claim 1, wherein said polyclonal antibody is prepared with pepsin-solubilized human type IV collagen as the antigen.

6. The method according to claim 1, wherein said sample is a body fluid.

7. The method according to claim 6, wherein said body fluid is blood serum.

8. A kit for immunoassay of human type IV collagen, which kit comprises
   (1) a carrier immobilized monoclonal antibody against human type IV collagen or said monoclonal antibody and an immobilizing carrier therefor; and
   (2) labelled polyclonal antibody against type IV collagen, wherein said monoclonal antibody is produced by a mouse X mouse hybridoma COL IV-67 (FERM BP-5240) and wherein said monoclonal antibody;
   (1) is raised against pepsin-solubilized human type IV collagen, said type IV collagen having been purified at least with DEAE agarose;
   (2) binds to the 7S domain of human type IV collagen but not to other domains;
   (3) does not bind to human type I, type III and type V collagen;
   (4) when analyzed by SDS-polyacrylamide gel electrophoresis under reduced condition, comprises a heavy (H) chain of about 51,000 daltons and a light (L) chain of about 28,000 daltons; and
   (5) is of the IgG1κ subtype.

9. A kit according to claim 8, wherein said polyclonal antibody is an antibody against pepsin-solubilized human type IV collagen.

10. A kit according to claim 8, wherein said carrier is a solid carrier.

11. A method for immunoassay of human type IV collagen in a sample, comprising contacting a sample with a carrier immobilized monoclonal antibody against human type IV collagen and a labelled polyclonal antibody against human type IV collagen, wherein said monoclonal antibody is produced by a mouse X mouse hybridoma COL IV-238 (FERM BP-5239) and wherein said monoclonal antibody:
   (1) is raised against pepsin-solubilized human type IV collagen, said type IV collagen having been purified at least with DEAE agarose;
   (2) binds to domains other than the 7S domain of human type IV collagen but does not bind to the 7S domain;
   (3) does not bind to human type I, type III and type V collagen;
   (4) when analyzed by SDS-polacrylamide gel electrophoresis under reduced condition, comprises a heavy (H) chain of about 50,000 daltons and light (L) chain of about 27,000 daltons; and
   (5) is of the IgG2κ subtype; and
   detecting said human type IV collagen is said sample.

12. The method according to claim 11, further comprising steps wherein the carrier with monoclonal antibody against human type IV collagen is immobilized, the labelled polyclonal antibody against human type IV collagen and the sample are mixed together, the labelled polyclonal antibody bound to the carrier through the human type IV collagen in the sample is separated from the unbound labelled polyclonal antibody, and when in cases where an arbitrary amount of the labelled polyclonal antibody has been used, the amount of the label bound to the carrier is measured, whereas if a known amount of the labelled polyclonal antibody has been used, the amount of the label either bound or unbound to the carrier is measured.

13. The method according to claim 12, wherein said carrier is a solid carrier, and the separation of the label which is bound and unbound to the carrier is performed by separating the insoluble solid carrier from the reaction solution.

14. The method according to claim 11, wherein the label of said labelled polyclonal antibody is an enzyme, and said detecting of said human type IV collagen in said sample is made on the basis of the action of said enzyme against a substrate of said enzyme.

15. The method according to claim 11, wherein said polyclonal antibody is prepared with pepsin-solubilized human type IV collagen as the antigen.

16. The method according to claim 11, wherein said sample is a body fluid.

17. The method according to claim 16, wherein said body fluid is blood serum.

18. A kit for immunoassay of human type IV collagen, which kit comprises;
   (1) a carrier immobilized monoclonal antibody against human type IV collagen or said monoclonal antibody and an immobilizing carrier therefor; and
   (2) labelled polyclonal antibody against type IV collagen, wherein said monoclonal antibody is produced by a mouse X mouse hybridoma COL IV-238 (FERM BP-5239) and wherein said monoclonal antibody:
      (1) is raised against pepsin-solubilized human type IV collagen, said type IV collagen having been purified at least with DEAE agarose;
      (2) binds to domains other than the 7S domain of human type IV collagen but does not bind to the 7S domain;
      (3) does not bind to human type I, type III and type V collagen;
      (4) when analyzed by SDS-polyacrylamide gel electrophoresis under reduced condition, comprises a heavy (H) chain of about 50,000 daltons and a light (L) chain of about 27,000 daltons; and
      (5) is of the IgG2κ subtype.

19. A kit according to claim 18, wherein said polyclonal antibody is an antibody against pepsin-solubilized human type IV collagen.

20. A kit according to claim 18, wherein said carrier is a solid carrier.

21. A monoclonal antibody against human type IV collagen, wherein said monoclonal antibody is produced by a mouse X mouse hybridoma COL IV-67 (FERM BP-5240) and wherein said monoclonal antibody:
   (1) is raised against pepsin-solubilized human type IV collagen, said type IV collagen having been purified at least with DEAE agarose;
   (2) binds to the 7S domain of human type IV collagen but not to other domains;
   (3) does not bind to human type I, type III and type V collagen;
   (4) when analyzed by SDS-polyacrylamide gel electrophoresis under reduced condition, comprises a heavy (H) chain of about 51,000 daltons and a light (L) chain of about 28,000 daltons; and
   (5) is of the IgG1κ subtype.

22. A monoclonal antibody against human type IV collagen, wherein said monoclonal antibody is produced by a mouse X mouse hybridoma COL IV-238 (FERM BP-5239) and wherein said monoclonal antibody:
   (1) is raised against pepsin-solubilized human type IV collagen, said type IV collagen having been purified at least with DEAE agarose;
   (2) binds to domains other than the 7S domain of human type IV collagen but does not bind to the 7S domain;
   (3) does not bind to human type I, type III and type V collagen;
   (4) when analyzed by SDS-polyacrylamide gel electrophoresis under reduced condition, comprises a heavy (H) chain of about 50,000 daltons and a light (L) chain of about 27,000 daltons; and
   (5) is of the IgG2κ subtype.

* * * * *